(12) United States Patent
Bach et al.

(10) Patent No.: US 10,857,392 B2
(45) Date of Patent: Dec. 8, 2020

(54) SYSTEM AND METHOD FOR IN-LAYER SYNCHRONIZATION FOR FAST SPOT RESCANNING

(71) Applicants: Varian Medical Systems Particle Therapy GmbH., Troisdorf (DE); Varian Medical Systems, Inc., Palo Alto, CA (US)

(72) Inventors: Markus Bach, Overath (DE); Isabel Huth, Kuerten (DE); Juergen Heese, Cologne (DE); Franko Piskulich, Claremont, CA (US); Lei Dong, San Diego, CA (US)

(73) Assignees: Varian Medical Systems, Inc., Palo Alto, CA (US); Varian Medical Systems Particle Therapy GmbH, Troisdorf (DE)

( * ) Notice: Subject to any disclaimer, the term of this patent is extended or adjusted under 35 U.S.C. 154(b) by 164 days.

(21) Appl. No.: 15/786,392

(22) Filed: Oct. 17, 2017

(65) Prior Publication Data

US 2018/0036556 A1 Feb. 8, 2018

Related U.S. Application Data

(63) Continuation of application No. 15/087,800, filed on Mar. 31, 2016, now Pat. No. 9,789,342.

(60) Provisional application No. 62/163,302, filed on May 18, 2015.

(51) Int. Cl.
*A61N 5/10* (2006.01)

(52) U.S. Cl.
CPC ......... *A61N 5/1081* (2013.01); *A61N 5/1067* (2013.01); *A61N 5/1068* (2013.01); *A61N 5/1037* (2013.01); *A61N 5/1044* (2013.01); *A61N 5/1049* (2013.01); *A61N 2005/1087* (2013.01)

(58) Field of Classification Search
CPC .. A61N 5/1049; A61N 5/1067; A61N 5/1048; A61N 5/107; A61N 5/1037; A61N 5/1064; A61N 5/1069; A61N 5/1065; A61N 5/1068; A61B 5/7285; A61B 5/7292

See application file for complete search history.

(56) References Cited

U.S. PATENT DOCUMENTS

| | | |
|---|---|---|
| 5,866,912 A | 2/1999 | Slater et al. |
| 8,632,448 B1 | 1/2014 | Schulte et al. |
| 8,963,108 B2 | 2/2015 | Matteo et al. |

(Continued)

FOREIGN PATENT DOCUMENTS

| | | |
|---|---|---|
| EP | 2146354 | 1/2010 |
| WO | WO 2014155232 A1 | 10/2014 |

*Primary Examiner* — Brooke Purinton

(57) ABSTRACT

To overcome the difficulties inherent in conventional proton therapy systems, new techniques are described herein for synchronizing the application of proton radiation with the periodic movement of a target area. In an embodiment, a method is provided that combines multiple rescans of a spot scanning proton beam while monitoring the periodic motion of the target area, and aligning the applications of the proton beam with parameters of the periodic motion. For example, the direction(s) and frequency of the periodic motion may be monitored, and the timing, dose rate, and/or scanning direction and spot sequence of the beam can be adjusted to align with phases in the periodic motion.

20 Claims, 6 Drawing Sheets

(56) References Cited

U.S. PATENT DOCUMENTS

| | | | |
|---|---|---|---|
| 9,084,887 B2 | 7/2015 | Schulte et al. | |
| 2008/0144772 A1* | 6/2008 | Yi | A61N 5/1049 |
| | | | 378/65 |
| 2008/0191142 A1 | 8/2008 | Pedroni | |
| 2010/0301235 A1* | 12/2010 | Bert | A61N 5/103 |
| | | | 250/492.3 |
| 2011/0105821 A1* | 5/2011 | Dieter | A61N 5/1043 |
| | | | 600/1 |
| 2011/0297849 A1* | 12/2011 | Bert | A61N 5/10 |
| | | | 250/492.1 |
| 2012/0119115 A1* | 5/2012 | Iwata | A61B 5/08 |
| | | | 250/492.3 |
| 2012/0228521 A1* | 9/2012 | Honda | A61N 5/1043 |
| | | | 250/492.3 |
| 2013/0211482 A1* | 8/2013 | Piipponen | A61N 5/1049 |
| | | | 607/100 |
| 2014/0121442 A1* | 5/2014 | Matteo | A61N 5/1081 |
| | | | 600/1 |
| 2015/0099917 A1 | 4/2015 | Bula et al. | |
| 2015/0217139 A1* | 8/2015 | Bert | A61N 5/1043 |
| | | | 600/1 |
| 2015/0306424 A1* | 10/2015 | Bert | A61N 5/1037 |
| | | | 600/1 |
| 2016/0016010 A1 | 1/2016 | Schulte et al. | |

* cited by examiner

100

400

Exemplary Computer System 600

SYSTEM AND METHOD FOR IN-LAYER SYNCHRONIZATION FOR FAST SPOT RESCANNING

CLAIM OF PRIORITY AND RELATED U.S. APPLICATIONS

This application is a continuation of U.S. application Ser. No. 15/087,800, filed Mar. 31, 2016, now U.S. Pat. No. 9,789,342, which claims the benefit of U.S. Provisional Patent Application No. 62/163,302, filed May 18, 2015, both of which are incorporated herein by reference in their entirety.

TECHNICAL FIELD

Embodiments of this invention relate generally to directed irradiated particle beam applications. More specifically, embodiments of this invention are directed to improved methods and systems for directing a beam of irradiated particles to achieve a target dosage while accounting for target movement.

BACKGROUND

Proton therapy is a type of external beam radiation therapy that is characterized by the use of a beam of protons to irradiate diseased tissue. A chief advantage of proton therapy over other conventional therapies such as X-ray or neutron radiation therapies is that proton radiation has the ability to stop in matter—treatment dosages are applied as a sequence of proton beams with several energies three-dimensionally. The dose deposition of each monoenergetic, thin ("pencil") proton beam in a medium is characterized by a sharp increase in dose deposition (Single Bragg Peak) directly before the end of the proton range (i.e. beam depth), and thereby limiting the inadvertent exposure of non-target cells to potentially harmful radiation. The pencil beam scanning technique allows the deflection of monoenergetic proton beams to prescribed voxels (in transversal direction/ x- and y-coordinates for associated beam depths) in medium—the so called spot scanning technique (e.g., a "raster scan" of applications). Prescribed spot positions for a scanned proton beam delivery are typically arranged on a fixed (raster) pattern for each energy and therefore deliverable on a fixed scanning path within an energy layer (for example on a meander like path). By superposition of several proton beams of different energies, a Bragg peak can be spread out to cover target volumes by a uniform, prescribed dose. This enables proton therapy treatments to more precisely localize the radiation dosage relative to other types of external beam radiotherapy. During proton therapy treatment, a particle accelerator such as a cyclotron or synchrotron is used to generate a beam of protons from, for example, an internal ion source located in the center of the cyclotron. The protons in the beam are accelerated (via a generated electric field), and the beam of accelerated protons is subsequently "extracted" and magnetically directed through a series of interconnecting tubes (called a beamline), often through multiple chambers, rooms, or even floors of a building, before finally being applied through an end section of beamline (called Nozzle) to a target volume in a treatment room.

As the volumes (e.g., organs, or regions of a body) targeted for radiation therapy are often below the surface of the skin and/or extend in three dimensions, and since proton therapy—like all radiation therapies—can be harmful to intervening tissue located in a subject between the target area and the beam emitter, the precise calculation and application of correct dosage amounts and positions are critical to avoid exposing non target areas to the radiation beyond what is necessary. However, target volumes within a body can shift and move periodically and even subconsciously or involuntarily, due to its role in or proximity to a normal respiratory or cardiac cycle, for example. Unfortunately, this movement can cause an unintended application of a proton therapy beam to neighboring healthy tissues (and/or organs at risk) for proton beams initially planned to treat the target volume. Typically the total prescribed target dose for a radiation treatment is delivered in multiple equivalent weighted fractions (total target dose divided in multiple portions of equivalent dose).

As a solution to this issue, techniques have been developed that mitigate the deviation of actual versus prescribed dose distributions caused by target volumes moving during applications of proton beams. One such technique is rescanning for pencil beam spot scanning technique, in which the intended (target) dose to a voxel in the target volume is gained by repeated application of multiple portions of its prescribed target dose for a fraction (i.e. visiting the voxel several times in a sequence—called rescanning). Typically, each prescribed spot position in a depth of a target volume (characterized by a dedicated energy of proton beam) can be visited multiple times (have multiple re-scans) to ensure (to the extent possible) that the entirety of the target area is treated. Also, by increasing the number of rescans (dividing the dosage into smaller fractions), the potential harm from overexposing a point in or neighboring the target volume can be minimized. Multiple rescanning provides an improvement over traditional approaches, particularly for the center of a target area. However, some issues still arise from the movement of the target area that occurs simultaneously with a rescanned proton beam application on a rigid path with fixed timing parameters and dose rate variability between layers only. For example, parts of the dose amounts planned for the target volume can still be blurred or smeared in or around the perimeters of target areas.

SUMMARY

This Summary is provided to introduce a selection of concepts in a simplified form that is further described below in the Detailed Description. This Summary is not intended to identify key features or essential features of the claimed subject matter, nor is it intended to be used to limit the scope of the claimed subject matter.

To overcome the difficulties inherent in conventional proton therapy systems, new techniques are described herein for synchronizing the application of proton radiation with the periodic movement of a target area. In an embodiment, a method is provided that combines multiple rescans of a spot scanning proton beam while monitoring the periodic motion of the target area, and aligning the applications of the proton beam with parameters of the periodic motion. For example, the direction(s) and frequency of the periodic motion may be monitored, and the timing, dose rate, and/or scanning direction of the beam can be adjusted to align with phases in the periodic motion.

In one or more embodiments, alignment of the beam application with the periodic motion can be implemented according to various methods. For example, the timing of a beam application can be adjusted to align with phases in the periodic motion by artificially adding pauses or delays to a timed sequence of beam applications according to a radiation plan. Likewise, the scan direction and sequence of prescribed spot positions can be adjusted to align with phases in the periodic motion and to complement the motion of the target area for each phase. According to further embodiments, applications may also be aligned with the periodic motion of a target area by adjusting the dose rate of a beam application, for example by introducing a dose rate variability for consecutive beam on phases (for gated treatment) or even use a dose rate dynamic from spot to spot within a delivered proton energy layer.

According to another embodiment, a system is provided that is operable to perform the methods for aligning applications of a particle radiation beam (such as a proton therapy beam) with the motion of a target area. In an embodiment, a system is provided that includes a gantry that receives a stream of protons from a radiation source (such as a cyclotron or synchrotron) and is operable to rotate around a resting subject. Beam applications are emitted from a beam emitter or treatment nozzle attached to the gantry at pre-configured intensities and dose rates. The system also includes one or more sensors to monitor a motion of a target area in the subject. In one or more embodiments, the route traveled by the gantry, the position and direction of a beam emitted by the treatment nozzle—along with the sequential timing and/or dose rate of beam applications—can be dynamically aligned with the motion of the target area.

Further embodiments provide a set of programmed instructions implemented on a computer readable medium and executable by a processor in a computing device (such as a scan controller in a treatment system). In one or more embodiments, one or more of the gantry route, scan direction, spot sequence, dose rate, timing, and number of rescans for a session of beam applications is pre-calculated for a target area as a radiation plan (e.g., a proton treatment plan). Based on motion data received for the target area from one or more sensors, the parameters of the proton treatment plan for a session may be dynamically adjusted to align the application with the periodic motion of the target area.

By utilizing the systems and methods described above, the application of irradiated particles (such as protons) can be directed with greater precision by aligning beam applications with the periodic motion of a target area. Through the resulting synchronization, misdirected or misapplied beam applications can be effectively reduced.

BRIEF DESCRIPTION OF DRAWINGS

The accompanying drawings, which are incorporated in and form a part of this specification, illustrate embodiments of the disclosure and, together with the description, serve to explain the principles of the presently claimed subject matter:

DETAILED DESCRIPTION

Figure 1:
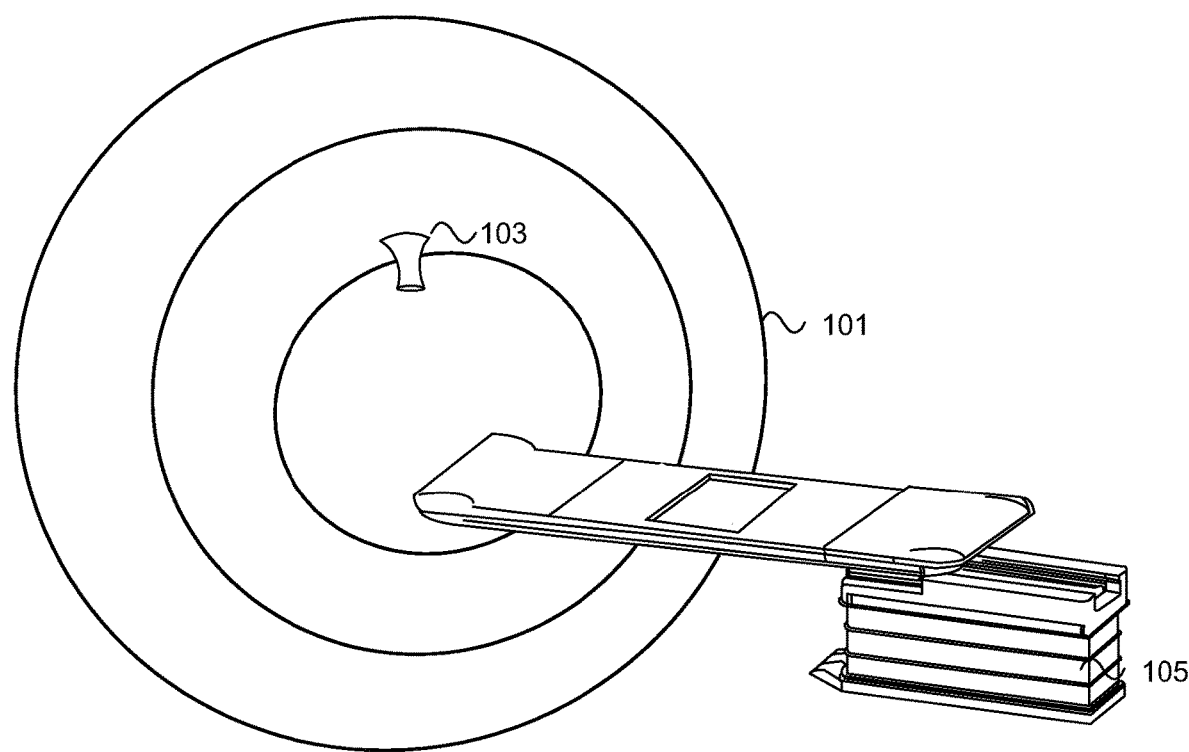
FIG. 1 depicts an exemplary proton therapy device in accordance with embodiments of the present disclosure.

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known processes, procedures, components, and circuits have not been described in detail as not to unnecessarily obscure aspects and features of the subject matter.

Portions of the detailed description that follow are presented and discussed in terms of a process. Although operations and sequencing thereof are disclosed in a figure herein (e.g., FIG. 2) describing the operations of this process, such operations and sequencing are exemplary. Embodiments are well suited to performing various other operations or variations of the operations recited in the flowchart of the figure herein, and in a sequence other than that depicted and described herein.

Some portions of the detailed description are presented in terms of procedures, operations, logic blocks, processing, and other symbolic representations of operations on data bits that can be performed on computer memory. These descriptions and representations are the means used by those skilled in the data processing arts to most effectively convey the substance of their work to others skilled in the art. A procedure, computer-executed operation, logic block, process, etc., is here, and generally, conceived to be a self-consistent sequence of operations or instructions leading to a desired result. The operations are those requiring physical manipulations of physical quantities. Usually, though not necessarily, these quantities take the form of electrical or magnetic signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout, discussions utilizing terms such as "accessing," "writing," "including," "storing," "transmitting," "traversing," "associating," "identifying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

While the following example configurations are shown as incorporating specific, enumerated features and elements, it is understood that such depiction is exemplary. Accordingly, embodiments are well suited to applications involving different, additional, or fewer elements, features, or arrangements.

In-Layer Synchronization for Fast Spot Scanning

The claimed subject matter is directed to a particle beam control system. In an embodiment, the beam control system may be implemented in conjunction with one or more treatment or application stations operable to receive a stream of particles from a source, an integrated beam control panel or display, executed as computer-implemented graphical interfaces associated with one or more treatment rooms. Alternately, the beam control system may also be implemented as a single, dedicated beam control panel and graphical interface, such as when a cyclotron is dedicated to a single treatment room and not shared between multiple treatment rooms. The beam control system as described may be configured as a distributed system to provide customized graphical visualizations of a treatment session that includes one or more beam fields arranged for one or more beam applications, and integrated displays and control for a delivery of the beam for single or grouped beam fields to a beam control system.

According to further embodiments, the beam control system (through the beam control display, for example) may also graphically present beam status information for beam applications submitted by a user, such as the beam field delivery order of the grouped fields. In addition, the beam control interface may also provide controls for the user to add or remove beam fields to and from a beam field grouping. According to some embodiments, the display contents and controls indicate beam field grouping functions and treatment statuses via graphical or numeric means. According, the display and integrated controls can be significantly, if not completely, language-independent.

According to one or more embodiments, beam delivery control can be provided remotely with respect to both the source of the particle beam, as well as from the treatment room itself. As recited herein, a beam is defined as a proton therapy beam or other irradiated particle beam used for radiation application such as therapy treatment. Each session may itself contain one or more treatment (beam) fields—the areas targeted by a beam during a portion or entirety of a treatment. The fields may be irradiated in a series of layers (i.e. energies), each layer having one or more "raster scans" (rescans) that direct an application of the beam in a short burst to one or more proximate points under a temporal and spatial, pre-calculated sequence. In one or more embodiments, the beam energy for a session may be calculated for the furthest depth that corresponds to the furthest layer in a target, and additional attenuating components such as collimators and jaws may be placed in the path of a beam during the session to apply the proton therapy to shallower layers.

Exemplary Radiation Therapy Device

FIG. 1 depicts an exemplary radiation therapy device 100 in a treatment therapy room, in accordance with various embodiments of the claimed subject matter. As presented in FIG. 1, radiation therapy device 100 includes a gantry 101, a radiation treatment nozzle 103, and a subject positioner 105. In one or more embodiments, the gantry 101 may comprise an opening through which at least a portion of the subject positioner 105 is able to enter (e.g., via automatic and/or mechanical means). In one or more embodiments, at least a portion of the gantry may be operable to rotate around the opening (typically while at least a portion of the subject positioner is disposed within). For example, as depicted in FIG. 1, the gantry 101 may be implemented as a ring, at least a portion of which may be rotatable around an axis bisected by the subject positioner 105.

According to one or more embodiments, the gantry 101 is configured to receive irradiated particles through a beam line connected to a particle accelerator (not shown). The particle accelerator may be implemented as, but is not limited to, a proton accelerator such as a cyclotron or synchrotron. In one or more embodiments, the particle accelerator may be positioned remotely with respect to the treatment therapy room and may be shared between multiple radiation therapy devices housed in multiple treatment therapy rooms. Beam lines (e.g., vacuum sealed tubes or pipes used to transfer irradiated particles) are used to connect the particle accelerator to each of the radiation therapy devices. The irradiated particles are emitted from the radiation therapy device 100 through the treatment nozzle 103 located on the gantry 101. In one or more embodiments, the treatment nozzle 103 is rotated about the opening of the gantry 101 through a rotation of at least a portion of the gantry. In alternate embodiments, movement of the treatment nozzle 103 may be performed via movement of one or more robotic appendages coupled to the gantry 101.

In one or more embodiments, the subject positioner 105 may include a support structure (such as a table, chair, bench, or bed) upon which a treatment subject may lie, sit, or rest upon. According to further embodiments, portions of the subject positioner 105 may be capable of movement, via automatic and/or mechanical means. For example, the incline of a portion of the resting surface may be increased or decreased (e.g., physically via a mechanism or automatically through a graphical user interface). Portions of the subject positioner 105 may also be equipped with means to rotate, extend, or retract. For example, according to one or more embodiments, a portion of the resting surface of the subject positioner 105 may be extended or physically positioned into an opening of the gantry 101, such that a treatment subject resting on the subject positioner 105 bisects the plane at which the treatment nozzle 103 is directed.

One or both of the gantry 101 and the subject positioner 105 is/are capable of maneuvering, either independently or in conjunction, to align a treatment subject positioned on the subject positioner 105 with a treatment nozzle 103. Movement of the gantry 101 and/or subject positioner 105 may include, but is not limited to, rotation, extension, retraction, contraction, adduction, abduction, etc. of one or more articulated surfaces or portions of the gantry 101, and/or subject positioner 105. In one or more embodiments, treatment nozzle 103 may also be capable of limited movement, via multi-axial rotation, for example. Movement of the gantry 101, treatment nozzle 103, and/or subject positioner 105 may be performed automatically, via pre-programmed instructions that correspond to optimized alignments for desired iso-centers, or may be controlled remotely via a user interface.

A treatment subject may be positioned (e.g., by lying prone) on a subject positioner 105 at an initial or starting position. One or more portions of the subject positioner 105 may extend towards an opening presented by the gantry 101, such that a target region of the treatment subject is aligned with a position of the treatment nozzle 103, located on or around an inner surface of the gantry 101. In alternate or further embodiments, the gantry 101 may also rotate in an arc around the circumference of the gantry 101 to position the treatment nozzle 103 to produce the desired beam field or to do position verification of a treatment subject positioned on a subject positioner 105. Once the gantry 101, treatment nozzle 103, and/or subject positioner 105 are aligned in the desired orientation, treatment therapy may begin. Specifically, an iso-center in the treatment subject may be aligned with the treatment nozzle 103 via movement of the gantry 101 and/or subject positioner 105. In one or more embodiments, treatment therapy may comprise the application of irradiated particles generated at a (remote) particle accelerator, received in the gantry 101, and emitted (e.g., as a raster scan) in a beam field from the treatment nozzle 103 at an iso-center located in a treatment subject according to a pre-determined treatment therapy plan.

The treatment nozzle 103 may be configured to emit the irradiated particles in a spot scanning beam (also referred to as a "pencil beam"). In specific embodiments of the invention, system 200 is capable of three-dimensional spot scanning because the energy level for protons in the proton beam is selected based on a depth of the target and the transversal coordinates of the beam can be adjusted by the scanning system. Adjusting the energy level of the beam allows control of the depth at which the Bragg Peak of the accelerated protons is located. The increased flexibility made available through three-dimensional spot scanning greatly improves the precision of the dose delivered to a patient so as to maximize dose delivery to a tumor and minimize damage to healthy tissue.

A spot-scanning beam may be produced by crossing two or more extracted beams at an extremely fine point in the radiation device. A target area (beam field) may be irradiated with a raster scan (two-dimensional emission) of the resultant spot scanning beam. In one or more embodiments, multiple beam fields sharing the same or proximate iso-centers may be irradiated with the spot scanning beam in a contiguous session, uninterrupted by application of the spot scanning beam to more distant or unrelated beam fields, for example. In further embodiments, beam fields that do not require the addition and/or removal of additional accessories such as (but not limited to) collimators, jaws, and range shifters, etc., may be irradiated in a contiguous beam application, as an automated treatment of a set of fields.

In one or more embodiments, a subject resting or positioned on the subject positioner may be monitored. For example, the motion of a target area within the subject may be monitored by, but is not limited to, continuous imaging the target volume and/or tracking one or more motion surrogates directly correlated to the motion and/or position of a target volume (not shown). These surrogates may include, for example, respiratory markers or ECG signals. Other methods for monitoring a target area may include, but are not limited to, implanted sensors, real-time imaging devices, or any other device suitable to monitor organ motion and/or the respiratory or cardiac cycle(s) of a subject. Monitoring of a target area may include measuring a frequency and duration of each phase or cycle of a periodic motion exhibited by the target area (e.g., displacement from a resting or default position) and the timing (e.g., duration) of transitions between phases. Monitoring of a target area may also include measuring the direction and the peak displacement from the resting or default position, mapped to phases of the periodic motion.

The monitored motion may be analyzed and the analyzed motion characteristics may be used, but are not limited, to adjust the timing, direction and sequence of directed particle beam radiation associated with prescribed radiation plans to better align beam applications to account for the motion exhibited by the target area. In one or more embodiments, the radiation plan may be stored with other radiation plans as a plurality of programmed instructions in a memory device of a controller (e.g., a computing device executing an application) of the radiation therapy device 100 and the emission of the beam of irradiated particles.

Synchronization of Spot-Scanning with Target Motion

Figure 2:
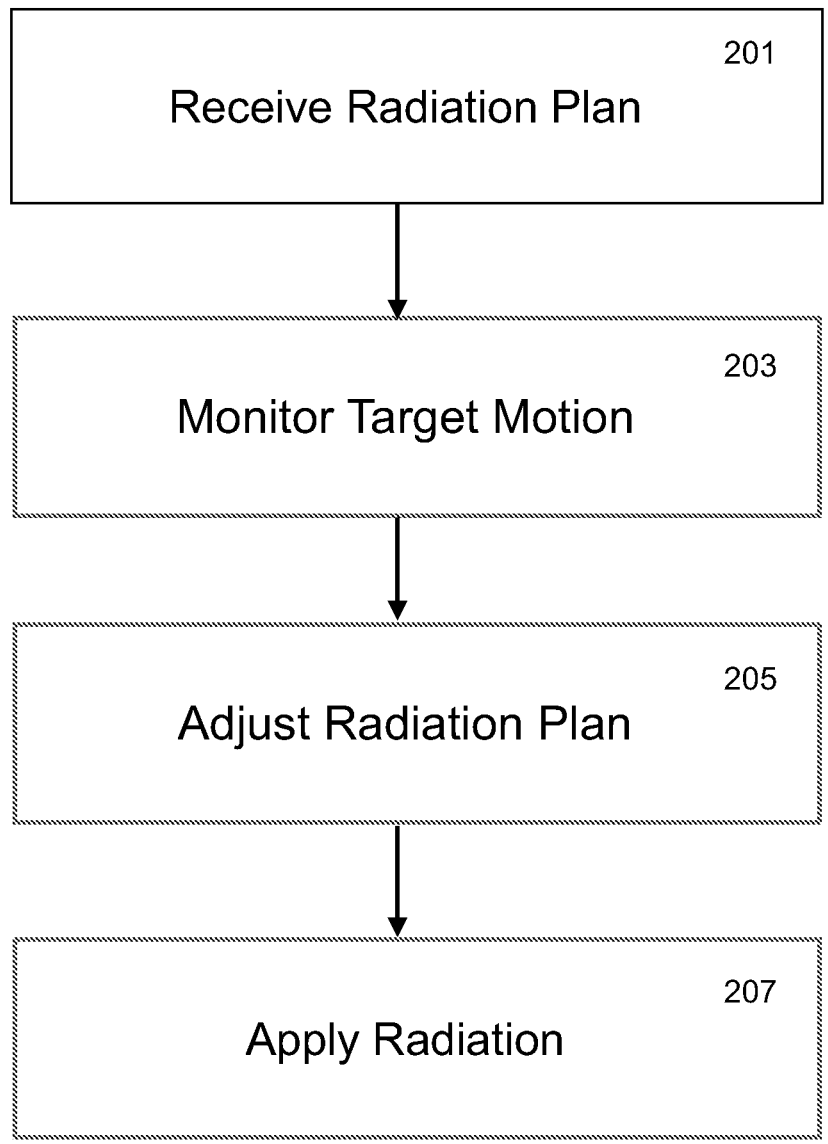
FIG. 2 depicts a flowchart of a process for aligning a radiation application session with a motion in a target area, in accordance with embodiments of the present disclosure.

FIG. 2 depicts a flow chart 200 of an exemplary process for synchronizing a spot-scanning proton beam with a target motion. Steps 201-207 describe exemplary steps comprising the process 200 depicted in FIG. 2 in accordance with the various embodiments herein described. In one embodiment, the process 200 is implemented in whole or in part as computer-executable instructions stored in a computer-readable medium and executed in a computing device.

At step 201, a radiation plan is received or accessed for a target area in a radiation subject. In one or more embodiments, the radiation plan may comprise a proton therapy plan for a patient undergoing radiation (proton-therapy) treatment. According to one or more embodiments, the radiation plan is received as data in a computing device executing an application operable to control a proton therapy treatment machine. The radiation plan may be pre-generated and associated with the radiation subject, and stored as one of a multitude of pre-generated records associated with a corresponding multitude of radiation subjects. In still further embodiments, the radiation plan may be include a timing sequence and position data for raster-scan applications of a spot-scanning proton beam during a treatment session.

At step 203, a motion of the target area is monitored. Motion of the target area may be monitored by, but is not limited to, continuous imaging the target volume and/or tracking one or more motion surrogates directly correlated to the motion and/or position of a target volume. In one or more embodiments, the motion may be monitored indirectly by monitoring a displacement of an adjacent field or object. Motion data is tracked using the sensors, and characteristics of periodic motions (e.g., inhalation and exhalation, heartbeats) exhibited by the target area are measured. These characteristics may include, for example, a frequency of a periodic motion, the duration of each phase in the periodic motion, and the timing of any transition period between each phase.

At step 205, the radiation plan received in step 201 is dynamically adjusted to align the timing sequences and position data of the raster-scan application with the periodic motion exhibited by the target area measured in step 203. Adjusting the radiation plan may be accomplished by a variety of beam and periodic motion characteristics. For example, a starting position of an application of a spot-scanning beam can be aligned with a phase of periodic movement such as a respiratory motion by altering the start position of each scan of a raster scan to begin at an arbitrary position within the target area during each phase in the periodic motion. A scanning direction of the spot-scanning beam application may be aligned to conform to the direction of the motion exhibited by the target area during a phase of periodic motion. The dose rate of a beam application can also be aligned with the periodic motion. For example, the dose rate of beam applications occurring during or near the transition periods between phases may be increased during periods of rest by the target area and decreased when the target area accelerates. Other characteristics of the beam may be aligned with the motion of the target area. For example, the number of raster scans may be increased or decreased by specifically mapping raster scans to phases.

In one or more embodiments, the beam applications may be gated around the periodic motion so that proton beam is not applied during or near transition periods or when the target area accelerates, or otherwise maximizes the application of the beam during periods of rest or constant motion. Gating around the periodic motion may be accomplished by adding artificial delays or pauses in the timing sequence of the radiation plan to delay application of the beam during transitions between phases, or even to pause applications during specific phases.

At step 207, the proton (e.g., spot-scanning) beam is applied according to the adjusted radiation plan determined at step 205. In one or more embodiments, the beam may be applied as a raster scan for one or more layers in a target area. In one embodiment, the scanning direction of the beam application is aligned at step 205 to complement the direction of the motion of the target area. For example, a target area may extend laterally during exhalation and retract during inhalation. A complementary raster scan may likewise reposition one of its scanning directions along the axis of the target volume motion. Likewise, if an application requires more time than available (for example by a duty cycle at using beam gating), a deliberate pause may be added to the raster scan (e.g., a duration of a complete cycle of the periodic motion). Thus, irradiations with scanned particles can be resumed when the target area is at the same position in space when the raster scan was paused before.

In one or more embodiments, steps 203 through 207 may be performed in real-time, such that the adjustment of a radiation plan and the application of a proton therapy beam may be aligned dynamically with the detected motion of a target area.

Figure 3A:
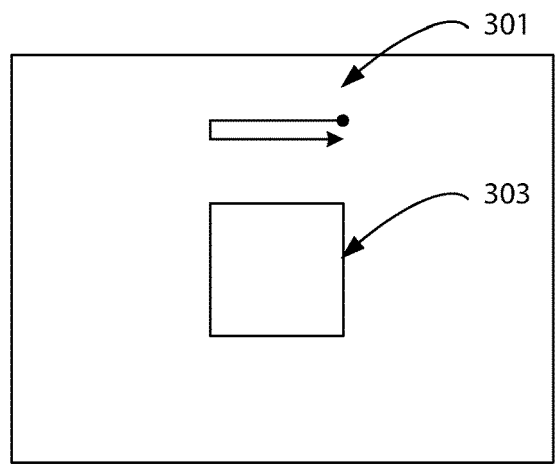
FIG. 3A depicts a first exemplary beam field for a motionless target area, in accordance with embodiments of the present disclosure.

In one or more embodiments, particles may be directed at the beam fields as a two-dimensional raster scan of proximate points in the target area. FIG. 3A depicts one such beam field (303). As depicted in FIG. 3A, the beam field 303 comprises a square with defined sides. Such a beam field 303 may be suitable for motionless or objects at rest, for example. In one or more embodiments, dosage from a spot-scanning proton beam may be applied to the beam field 303 in a series of sequential rows. As presented in FIG. 3A, a scanning direction 301 indicates the path through each row of the beam field 303 (e.g., moving left beginning from the upper right and snaking around).

Figure 3B:
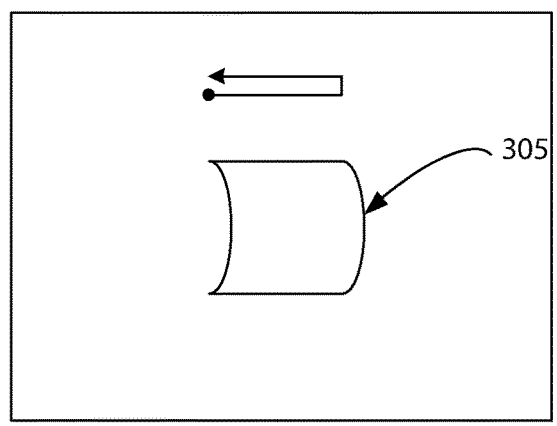
FIG. 3B depicts a second exemplary beam field for a target area moving laterally during a first phase of periodic motion, in accordance with embodiments of the present disclosure.

FIG. 3B depicts a second beam field (305) adjusted to align with the motion of a target area moving laterally (e.g., to the left of the default or resting position). As presented in FIG. 3B, the scanning direction and beginning position may be adjusted to begin when the target area is in between phases (e.g., immediately before exhalation) such that the scan mimics the motion of the target area as its displacement recedes to the beginning or resting position, and, after snaking around to the next row, likewise progresses to the left with the target area (e.g., during inhalation).

Figure 3C:
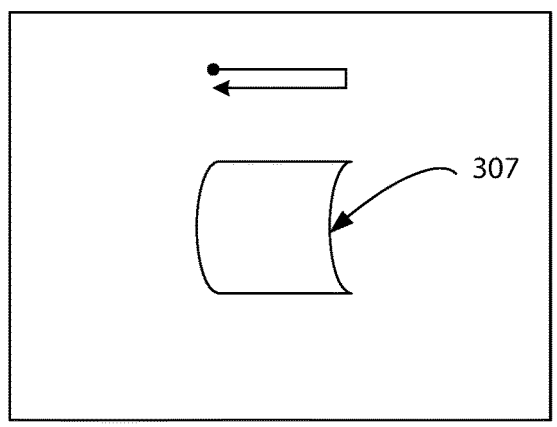
FIG. 3C depicts a third exemplary beam field for a target area moving laterally during a second phase of periodic motion, in accordance with embodiments of the present disclosure.

FIG. 3C depicts a third exemplary beam field (307) that is the opposite scenario to that depicted in FIG. 3B. As presented in FIG. 3C, the beam field (307) is adjusted to align with the motion of a target area moving laterally in the other direction (e.g., to the right from a default or resting position). As described above, a scanning direction and beginning position in a raster scan may likewise be adjusted to align with the motion and position of a target area. In the scenario depicted in FIG. 3C, a raster scan of a layer may begin when the target area leaves its resting position at the top left in the beam field, and may apply the spot-scanning beam moving right as the target area is displaced (e.g., during inhalation), and receding during the next phase in the cycle (e.g., exhalation).

The target dosage for an application session may be divided into (equal) fractions, and applied fractionally over the course of the raster scans such that the target dosage is still achieved cumulatively. According to one or more embodiments, the number of raster scans (and/or re-scans) may also be dynamically adjusted as necessary to achieve the target dosage.

Figure 4:
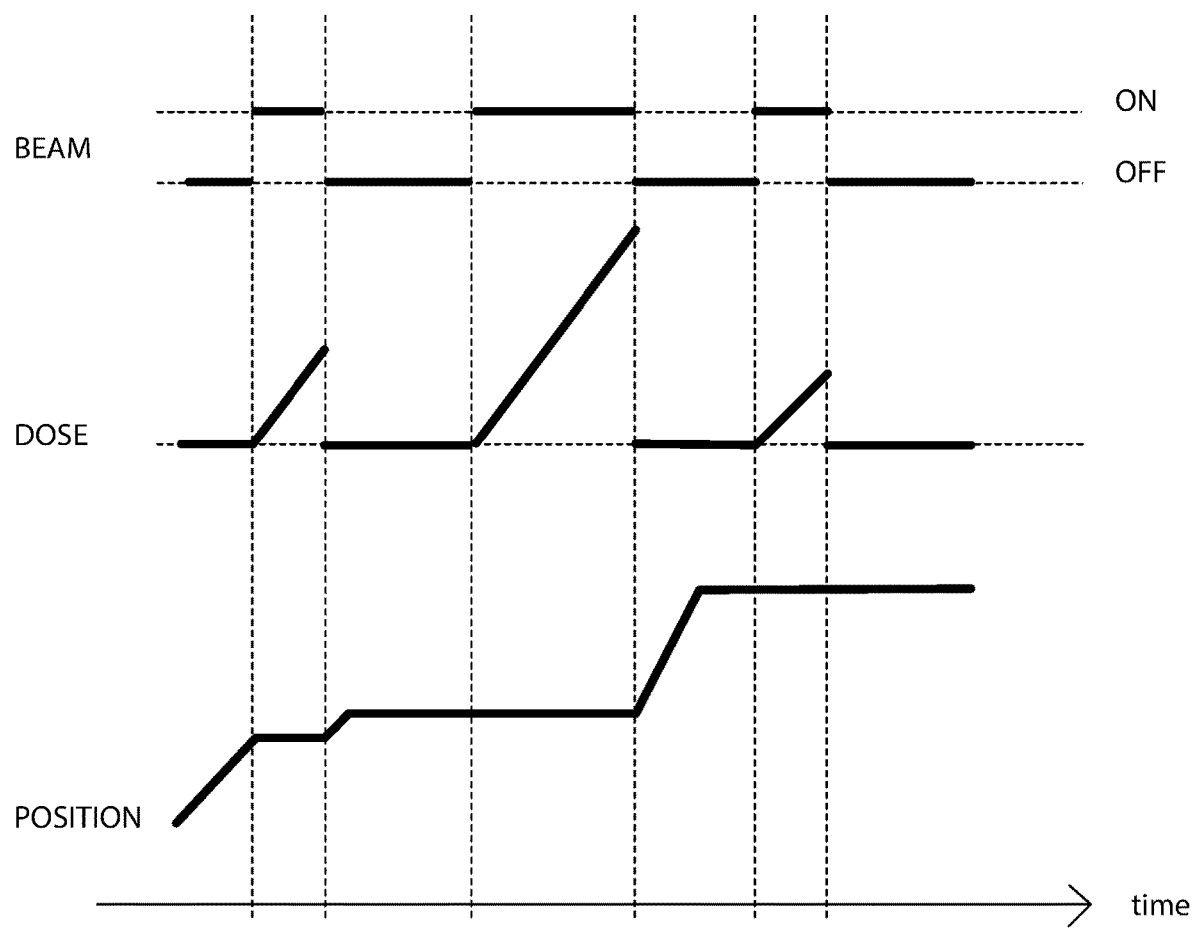
FIG. 4 depicts an exemplary first timing graph during a treatment session, in accordance with embodiments of the present disclosure.

In addition to the scan direction and starting positions, the application of the proton beam may be gated around the periodic motion of a target area. FIG. 4 depicts a timing graph (400) that plots a status of the beam, the dose rate of the beam, and the total distance traveled by the target area over time. As depicted in FIG. 4, the beam may be powered on and off to coincide with the motion of the target area. For example, when the distance traveled is level (e.g., the target area is not in motion) the beam may be powered on, as shown In FIG. 4. Likewise, when the position of the target area changes, the beam may be powered off. In one or more embodiments, the dose rate of the beam may also be dynamically adjusted to align with the target motion. For example, the dose rate can be increased to take advantage of longer periods of beam application—specifically, those that coincide with the target area being at rest.

Figure 5:
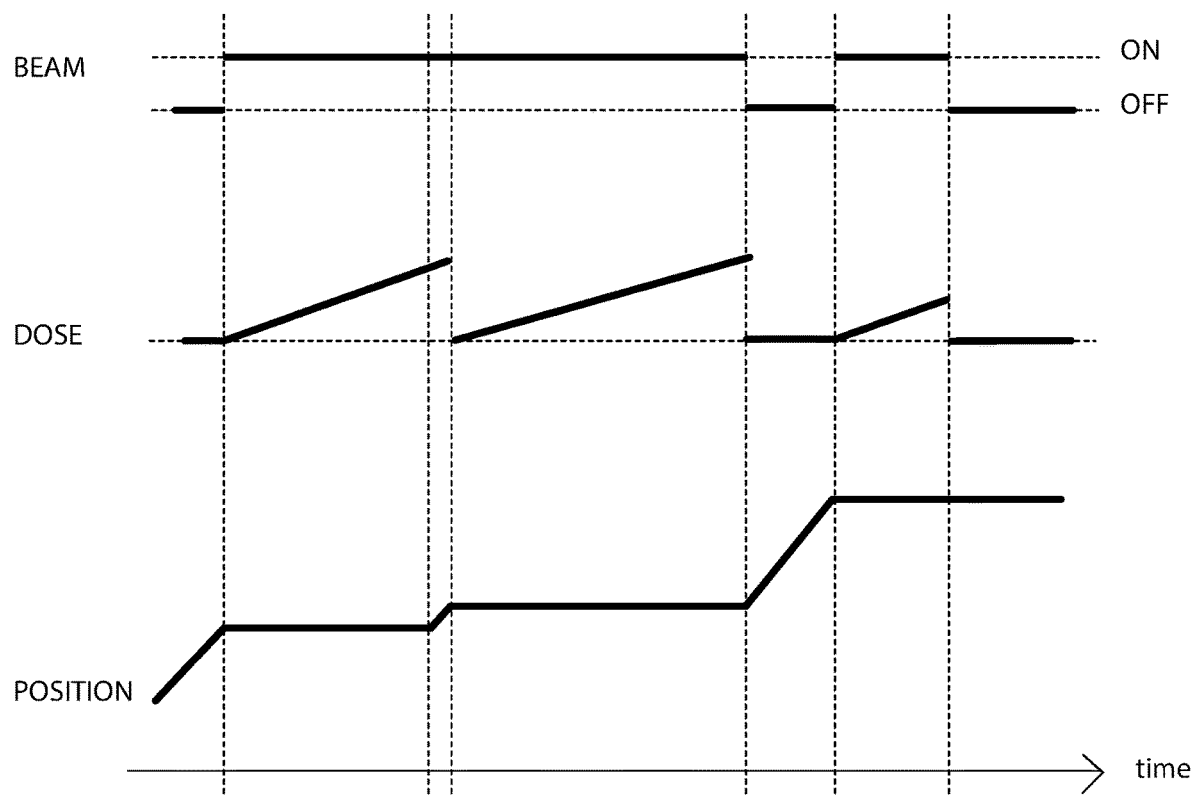
FIG. 5 depicts an exemplary second timing graph during a treatment session, in accordance with embodiments of the present disclosure.

Finally, the dose rate itself may be dynamically adjusted to coincide with the periodic motion of the target area. FIG. 5 depicts a second exemplary timing graph (500) that similarly plots the status of the beam, the dose rate of the beam, and the total distance traveled by the target area over time. As depicted in FIG. 5, the dose rate may decrease substantially (potentially even to zero) during periods of motion even while the beam is powered and being applied. Once motion in the target area discontinues, the dose rate may be increased over time.

By gating the application of the spot-scanning proton beam, and/or through alignment of the scanning position, scan direction, spot sequence and dose rate with the motion of a target area, sufficient coverage of the target area can be achieved with the target dosage without endangering neighboring tissue with misdirected or mistimed radiation.

Exemplary Computer System

Figure 6:
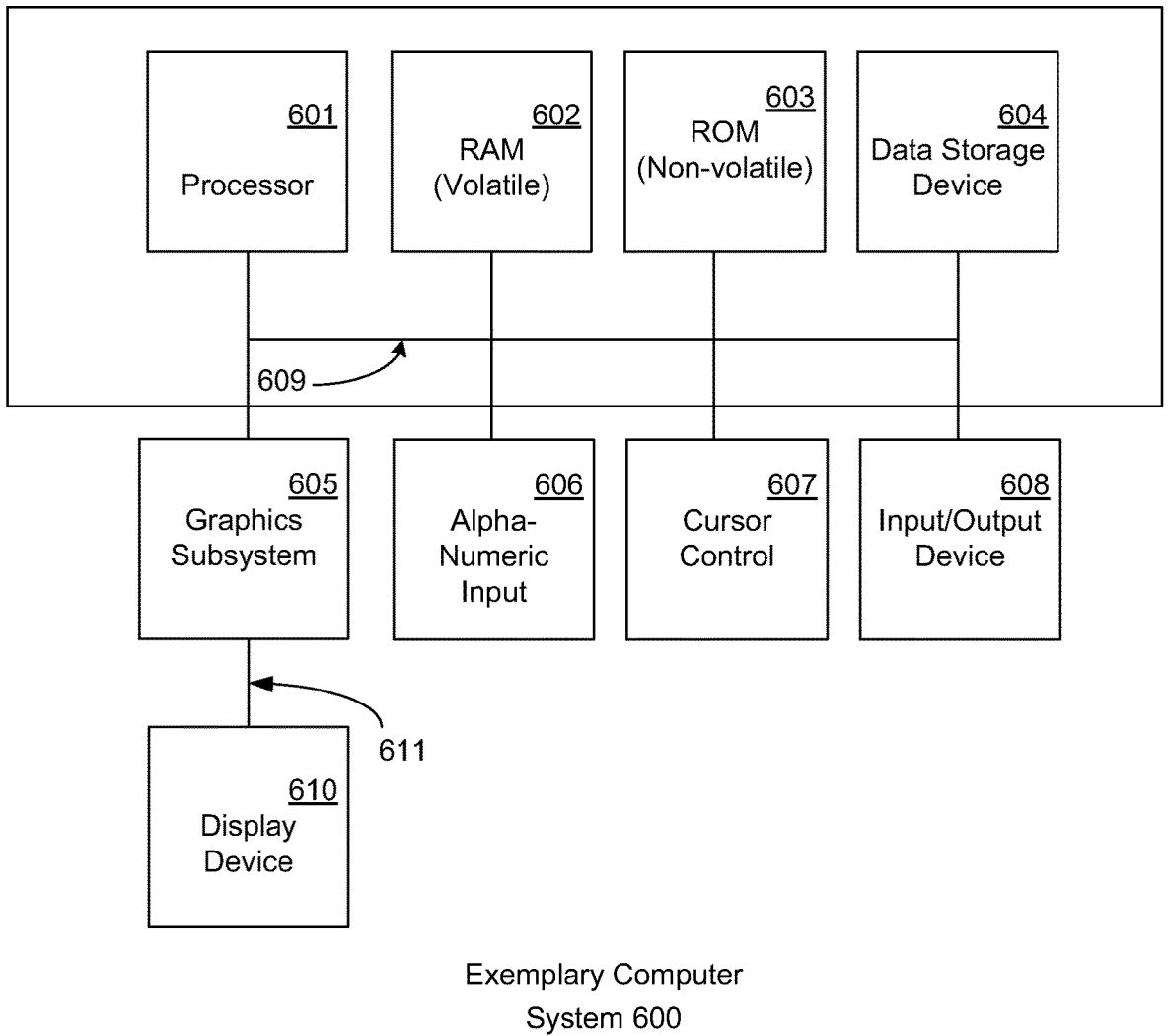
FIG. 6 depicts an exemplary computing environment, in accordance with embodiments of the present disclosure.

In one or more embodiments, alignment of the beam application with the motion of the target area may be executed as a series of programmed instructions executed on a computing environment operable to control the motion and emission of the radiation therapy machine described above with respect to FIG. 1. FIG. 6 depicts such a computing environment, including computing system 600 upon which embodiments of the present invention may be implemented includes a general purpose computing system environment. In its most basic configuration, computing system 600 typically includes at least one processing unit 601 and memory, and an address/data bus 609 (or other interface) for communicating information. Depending on the exact configuration and type of computing system environment, memory may be volatile (such as RAM 602), non-volatile (such as ROM 603, flash memory, etc.) or some combination of the two.

The computer system 600 may also comprise an optional graphics subsystem 605 for presenting information to the radiologist or other user, e.g., by displaying information on an attached display device 610, connected by a video cable 611. According to embodiments of the present claimed invention, the graphics subsystem 605 may be coupled directly to the display device 610 through the video cable 611. A graphical user interface of an application for grouping multiple beam fields may be generated in the graphics subsystem 605, for example, and displayed to the user in the display device 610. In alternate embodiments, display device 610 may be integrated into the computing system (e.g., a laptop or netbook display panel) and will not require a video cable 611.

Additionally, computing system 600 may also have additional features/functionality. For example, computing system 600 may also include additional storage (removable and/or non-removable) including, but not limited to, magnetic or optical disks or tape. Computer storage media includes volatile and nonvolatile, removable and non-removable media implemented in any method or technology for storage of information such as computer readable instructions, data structures, program modules or other data. RAM 602, ROM 603, and external data storage device (not shown) are all examples of computer storage media.

Computer system 600 also comprises an optional alphanumeric input device 606, an optional cursor control or directing device 607, and one or more signal communication interfaces (input/output devices, e.g., a network interface card) 608. Optional alphanumeric input device 606 can communicate information and command selections to central processor 601. Optional cursor control or directing device 607 is coupled to bus 609 for communicating user input information and command selections to central processor 601. Signal communication interface (input/output device) 608, also coupled to bus 609, can be a serial port. Communication interface 608 may also include wireless communication mechanisms. Using communication interface 608, computer system 600 can be communicatively coupled to other computer systems over a communication network such as the Internet or an intranet (e.g., a local area network).

In one or more embodiments, computing system 600 may be located in the same treatment room or suite as the radiation therapy device 100 described above with respect to FIG. 1. Alternately, computing system 600 may also be located externally with respect to the treatment room or suite containing treatment device 600.

By utilizing the systems and methods described above, the application of irradiated particles (such as protons) can be directed with greater precision by aligning beam applications with the periodic motion of a target area through the dynamic adjustment of beam characteristics and parameters. This alignment—all of which can be performed within a single, computing system—can effectively reduce misdirected, under-radiated, or misapplied beam applications and provide a more optimized treatment or radiation plan for radiation subjects.

Although the subject matter has been described in language specific to structural features and/or processological acts, it is to be understood that the subject matter defined in the appended claims is not necessarily limited to the specific features or acts described above. Rather, the specific features and acts described above are disclosed as example forms of implementing the claims.

What is claimed is:

1. A method for treatment of a target area with a radiation therapy beam, the method comprising:
    monitoring a position of the target area; and
    in response to detecting movements of the target area to different positions:
        aligning the radiation therapy beam to the different positions of the target area, wherein the movements of the target area comprise a plurality of phases of periodic movement; and
        administering a dosage to the different positions of the target area using the radiation therapy beam;
    wherein said administering a dosage to the different positions of the target area comprises applying the radiation therapy beam as a number of multiple raster scans over the target area, and wherein said aligning comprises adjusting the number of the multiple raster scans to conform to the phases of periodic movement.

2. The method of claim 1, wherein the radiation therapy beam comprises a spot scanning proton beam.

3. The method of claim 1, wherein the phases of periodic movement are delineated by a plurality of transition periods between the plurality of phases of periodic movement.

4. The method of claim 1, wherein said aligning further comprises an operation selected from the group consisting of:
    adjusting a dose rate of an application of the radiation therapy beam based on a phase of periodic movement; and
    gating applications of the radiation therapy beam outside of the phases of periodic movement, wherein the radiation therapy beam is not applied to the target area during transition periods between the phases of periodic movement.

5. The method of claim 1, wherein said aligning further comprises inserting a pause between administering a dosage to a position of the target area and said administering a dosage to a different position of the target area to synchronize application of the radiation therapy beam with a frequency of the movements of the target area.

6. The method of claim 1, wherein the movements of the target area comprise a movement of the target area selected from the group consisting of: a respiratory cycle; and a cardiac cycle.

7. The method of claim 1, wherein said administering further comprises applying the radiation therapy beam in a short burst to the target area.

8. The method of claim 1, wherein said aligning comprises an operation selected from the group consisting of: moving a nozzle through which the radiation therapy beam is emitted; moving a subject positioner on which a treatment subject containing the target area is positioned; and a combination of moving a nozzle through which the radiation therapy beam is emitted and moving a subject positioner on which a treatment subject containing the target area is positioned.

9. The method of claim 1, wherein said monitoring comprises an operation selected from the group consisting of: continuous imaging of the target area; and tracking a motion surrogate that is correlated to movement of the target area.

10. The method of claim 1, wherein said aligning comprises aligning a scanning direction of an application of the radiation therapy beam to conform to a direction of a movement exhibited by the target area during a phase of the periodic movement.

11. The method of claim 1, wherein said aligning comprises aligning a starting position of an application of the radiation therapy beam to conform to a direction of a movement exhibited by the target area during a phase of the periodic movement.

12. A system, comprising:
   a particle accelerator configured to produce a radiation therapy beam;
   a gantry configured to receive the radiation therapy beam and to rotate around a target subject;
   a nozzle configured to emit the radiation therapy beam at a target area in the target subject;
   a sensor device configured to monitor a movement of the target area; and
   a computing device configured to control motion and emission of the radiation therapy beam, wherein the computing device is operable for executing instructions stored in a readable medium, the instructions when executed performing a method comprising:
   monitoring positions of the target area; and
   in response to detecting movements of the target area to different positions:
      aligning the radiation therapy beam to the different positions of the target area, wherein the movements of the target area comprise a plurality of phases of periodic movement, and wherein said aligning comprises aligning a scanning direction of an application of the radiation therapy beam to conform to a direction of a movement exhibited by the target area during a phase of the periodic movement; and
      administering a dosage to the different positions of the target area using the radiation therapy beam;
   wherein said administering a dosage to the different positions of the target area comprises applying the radiation therapy beam as a number of multiple raster scans over the target area, wherein said aligning also comprises adjusting the number of multiple raster scans to conform to the phases of periodic movement.

13. The system of claim 12, wherein the radiation therapy beam comprises a spot scanning proton beam.

14. The system of claim 12, wherein the plurality of phases of periodic movement are delineated by a plurality of transition periods between the plurality of phases of periodic movement.

15. The system of claim 12, wherein said aligning further comprises an operation selected from the group consisting of:
   adjusting a dose rate of an application of the radiation therapy beam based on a phase of periodic movement; and
   gating applications of the radiation therapy beam outside of the phases of periodic movement, wherein the radiation therapy beam is not applied to the target area during transition periods between the phases of periodic movement.

16. The system of claim 12, wherein said aligning further comprises inserting a pause between administering a dosage to a position of the target area and said administering a dosage to a different position of the target area to synchronize application of the radiation therapy beam with a frequency of the movements of the target area.

17. The system of claim 12, wherein said administering further comprises applying the radiation therapy beam in a short burst to the target area.

18. The system of claim 12, wherein said aligning comprises an operation selected from the group consisting of: moving the nozzle; moving the gantry; moving a subject positioner on which a treatment subject containing the target area is positioned; and a combination of moving the nozzle, moving the gantry, and moving a subject positioner on which a treatment subject containing the target area is positioned.

19. The system of claim 12, wherein said monitoring comprises an operation selected from the group consisting of: continuous imaging of the target area; and tracking a motion surrogate that is correlated to movement of the target area.

20. The system of claim 12, wherein said aligning also comprises aligning a starting position of an application of the radiation therapy beam to conform to a direction of a movement exhibited by the target area during a phase of the periodic movement.

* * * * *